US011812989B2

(12) United States Patent
Shiraishi et al.

(10) Patent No.: US 11,812,989 B2
(45) Date of Patent: Nov. 14, 2023

(54) MEDICAL DEVICE

(71) Applicant: TERUMO KABUSHIKI KAISHA, Tokyo (JP)

(72) Inventors: Mizuho Shiraishi, Sagamihara Kanagawa (JP); Akihiro Takahashi, Matsuda Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 453 days.

(21) Appl. No.: 16/997,787

(22) Filed: Aug. 19, 2020

(65) Prior Publication Data
US 2020/0405345 A1 Dec. 31, 2020

Related U.S. Application Data

(63) Continuation of application No. PCT/JP2019/009731, filed on Mar. 11, 2019.

(30) Foreign Application Priority Data

Mar. 23, 2018 (JP) .................................. 2018-056006

(51) Int. Cl.
*A61B 17/3207* (2006.01)
*A61B 17/32* (2006.01)

(52) U.S. Cl.
CPC ............. *A61B 17/320758* (2013.01); *A61B 2017/320052* (2013.01); *A61B 2017/320064* (2013.01); *A61B 2217/005* (2013.01)

(58) Field of Classification Search
CPC .... A61B 17/320758; A61B 17/320725; A61B 17/32075; A61B 17/320783;
(Continued)

(56) References Cited

U.S. PATENT DOCUMENTS 6,024,749 A * 2/2000 Shturman ...... A61B 17/320758
606/159
6,129,734 A 10/2000 Shturman et al.
(Continued)

FOREIGN PATENT DOCUMENTS

JP 2016221081 A 12/2016

OTHER PUBLICATIONS

English Translation of International Search Report dated Jun. 11, 2019, mailed in counterpart International Application No. PCT/JP2019/009731, 1 page.

(Continued)

*Primary Examiner* — Tuan V Nguyen
(74) *Attorney, Agent, or Firm* — Kim & Stewart LLP

(57) ABSTRACT

A medical device for removing an object in a body lumen includes a catheter and a drive device. The drive device includes a hub support portion with which a hub portion of the catheter is interlocked. The hub portion has first and second engagement portions interlocked with the hub support portion. The hub support portion includes a rotation blocking portion that is engaged with the first engagement portion to block the hub portion from rotating with respect to the hub support portion, a movement blocking portion that is engaged with the second engagement portion to block movement of the hub portion with respect to the hub support portion in an axial direction, and a releasing portion that releases a state in which a rotation of the hub portion is blocked while maintaining a state in which movement of the hub portion is blocked.

16 Claims, 8 Drawing Sheets

(58) Field of Classification Search
CPC ... A61B 17/32002; A61B 2017/320775; A61F 9/00763
See application file for complete search history.

(56) References Cited

U.S. PATENT DOCUMENTS

| | | |
|---|---|---|
| 10,258,366 B2 | 4/2019 | Nakano et al. |
| 2017/0340401 A1 | 11/2017 | Miller et al. |

OTHER PUBLICATIONS

English Translation of Written Opinion dated Jun. 11, 2019, mailed in counterpart International Application No. PCT/ JP2019/009731, 4 pages.

* cited by examiner

MEDICAL DEVICE

CROSS-REFERENCE TO RELATED APPLICATION(S)

This application is a continuation of International Patent Application No. PCT/JP2019/009731, filed on Mar. 11, 2019, which is based upon and claims the benefit of priority from Japanese Patent Application No. 2018-056006, filed on Mar. 23, 2018, the entire contents of which are incorporated herein by reference.

BACKGROUND OF THE INVENTION

Field of the Invention

The present invention relates to a medical device for removing an object in a body lumen.

Background Art

Methods for treating a stenosed site due to plaque or thrombus in a blood vessel include a method of inflating the blood vessel with a balloon and a method of indwelling a mesh-like or coil-like stent in the blood vessel as a support for the blood vessel. However, it is difficult for these methods to treat the stenosed site that is hardened by calcification or a stenosed site that occurs at a branching portion of a blood vessel. A method that makes treatment possible even in such a case is atherectomy using which a stenosis object such as plaque and thrombus is cut and removed.

For example, "PERIPHERAL US PRODUCT CATALOG" (July 2017, p. 3 to 4, [searched on Mar. 7, 2018], Internet <URL: https://www.medtronic.com/content/dam/medtronic-com/products/cardiovascular/peripheral-therapies/documents/peripheral-us-product-catalog.pdf>) describes an atherectomy system including a catheter having a cutter for cutting a calcified lesion at a distal portion and a driver that transmits a driving force to the catheter. The rotating cutter is exposed at a side surface of the catheter. By changing its rotational position, this catheter is able to change the direction in which the cutter for cutting the calcified lesion is exposed.

When interlocking the catheter described in "PERIPHERAL US PRODUCT CATALOG" to the driver, the position of the catheter in the rotational direction needs to be aligned so that it is at the position at which the driver can be interlocked.

In a case where the position of the cutter of the catheter needs to be changed, the catheter and the driver are rotated together. However, since the driver is large relative to the catheter, it is difficult to perform this repositioning. Further, since the driver is rotated together with the catheter and the driver is rotated while it is at a more proximal position than the catheter and the cutter is located at the distal position of the catheter, it is difficult to transmit the torque for changing the position of the cutter.

In a case where the position of the cutter of the catheter needs to be changed before cutting the lesion, the catheter is rotated by a torque knob disposed on the proximal side of the catheter. Because the cutter is located at the distal position of the catheter, it is difficult to transmit the torque for changing the position of the cutter.

SUMMARY OF THE INVENTION

One or more embodiments solve the above-described problems, and provide a medical device capable of easily changing direction within a body lumen and removing an object in the body lumen.

A medical device for cutting an object in a body lumen, according to one or more embodiments includes: a catheter to be inserted into the body lumen; and a drive device interlocked with the catheter. The catheter includes a rotatable drive shaft, an outer tube in which the drive shaft is contained so as to be rotatable with respect thereto, a cutting portion for cutting the object, fixed to a distal portion of the drive shaft, and a hub portion fixed to a proximal portion of the outer tube and in which the drive shaft is contained so as to be rotatable with respect thereto. The drive device includes a drive unit interlocked with the drive shaft to transmit a rotational force to the drive shaft, and a hub support portion with which the hub portion is interlocked. The hub portion has first and second engagement portions interlocked with the hub support portion. The hub support portion includes a rotation blocking portion that is engaged with the first engagement portion to block the rotation of the hub portion with respect to the hub support portion, a movement blocking portion that is engaged with the second engagement portion to block the movement of the hub portion with respect to the hub support portion in an axial direction, and a releasing portion to be actuated to release a state in which the rotation of the hub portion is blocked while maintaining a state in which the movement of the hub portion in the axial direction is blocked.

In the medical device configured as described above, the hub portion can be rotatable with respect to the drive device while the movement of the hub portion with respect to the drive device is blocked in the axial direction, by actuating the releasing portion. Therefore, the position of the catheter in the body lumen can be easily changed by rotating the catheter without separating the hub portion from the drive device.

BRIEF DESCRIPTION OF THE DRAWINGS

FIG. 4A illustrates a state where the catheter is fixed to a drive device; FIG. 4B illustrates a state where the catheter is rotatably interlocked with the drive device; and FIG. 4C illustrates a state where the catheter can be detached from the drive device.

FIG. 5A illustrates a state where the catheter is fixed to the drive device; FIG. 5B illustrates a state where the catheter is rotatably interlocked with the drive device; and FIG. 5C illustrates a state where the catheter can be detached from the drive device.

FIG. 8A illustrates a state where the catheter is fixed to the drive device; and FIG. 8B illustrates a state where the catheter is rotatably interlocked with the drive device.

FIG. 9A is a cross-sectional view; and FIG. 9B is a plan view viewed from an arrow C in 9A.

FIG. 10A is a cross-sectional view; and 10B is a plan view viewed from an arrow D of 10A.

FIG. 11A is a cross-sectional view; and FIG. 11B is a plan view viewed from an arrow E of FIG. 11A.

DETAILED DESCRIPTION OF THE INVENTION

Figure 1:
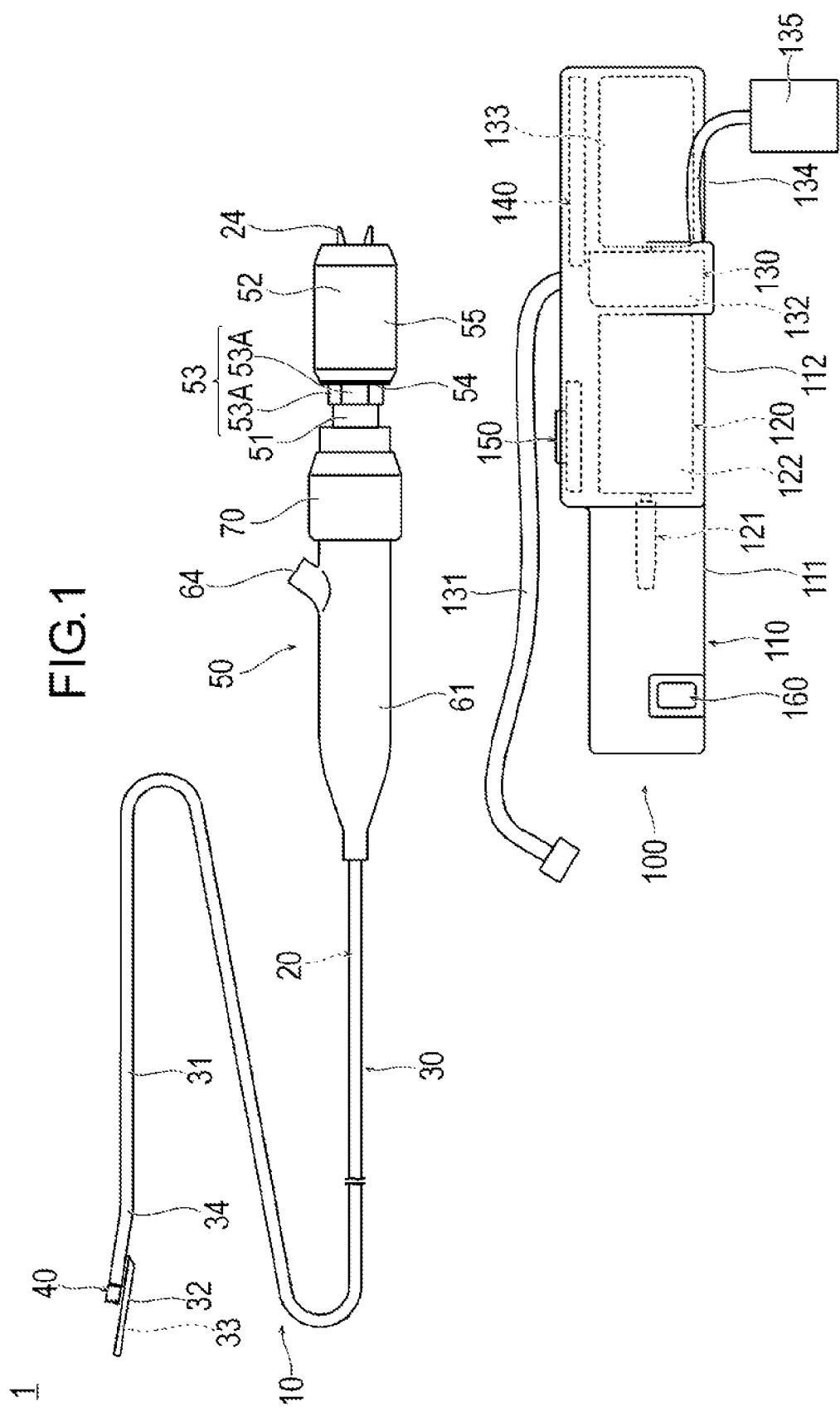
FIG. 1 is a plan view illustrating a medical device according to a first embodiment.

Hereinafter, embodiments will be described with reference to the drawings. In some cases, the sizes and ratios of the respective members in the drawings may be exaggerated for convenience of description and may differ from the actual sizes and ratios.

First Embodiment

In acute lower limb ischemia or deep venous thrombosis, a medical device 1 according to a first embodiment is inserted into a blood vessel and is used for a procedure to cut and remove thrombus, plaque, atheroma, calcified lesion, and the like. In the present specification, a side of the device which is inserted into a blood vessel is referred to as a "distal side", and a hand-side of the device which is operated by a user is referred to as a "proximal side". Further, an object to be removed is not necessarily limited to thrombus, plaque, atheroma, or calcified lesion, and may include any object that can be present in the body lumen.

Figure 2:
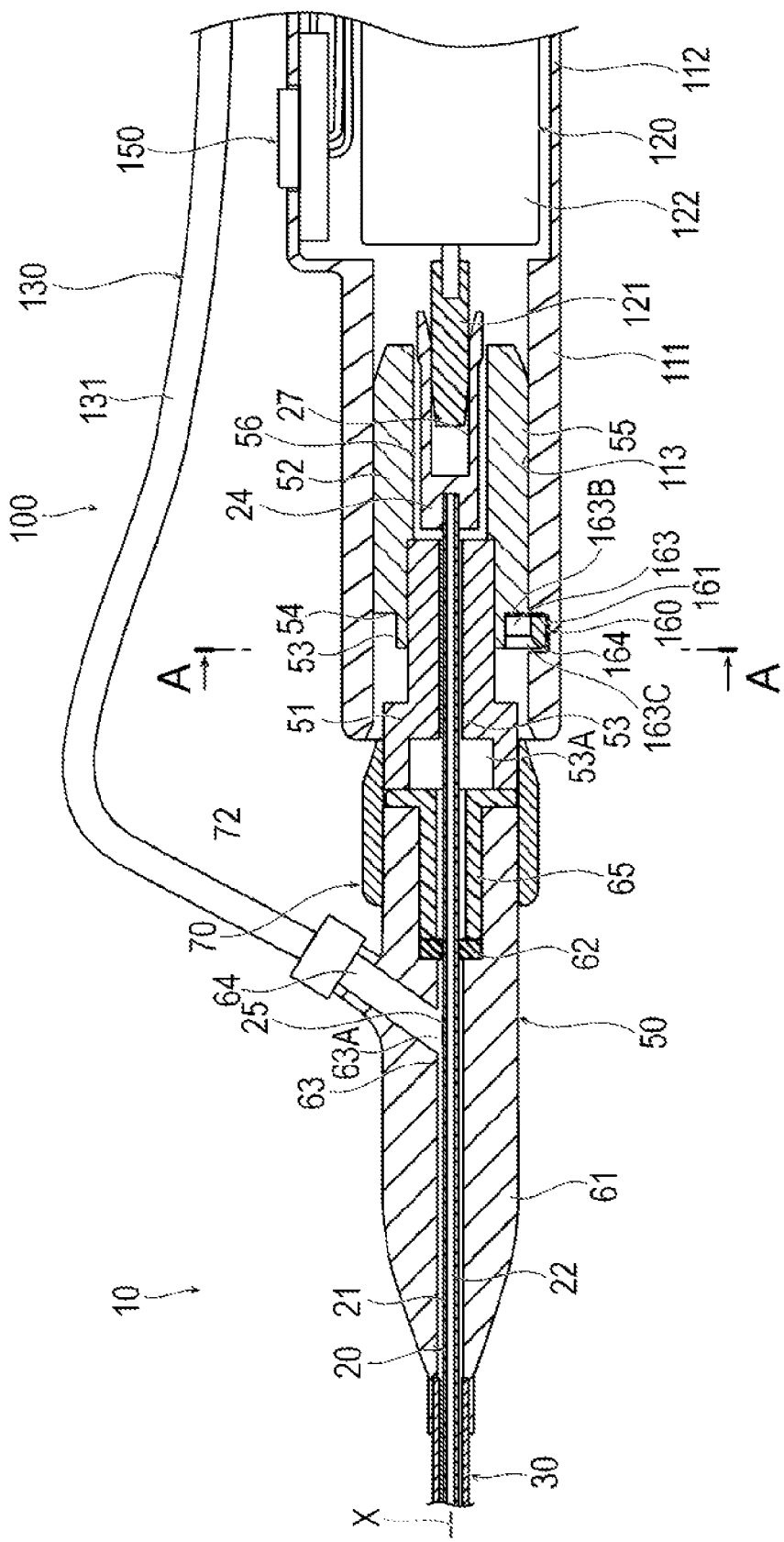
FIG. 2 is a cross-sectional view illustrating a proximal portion of a catheter.
Figure 3:
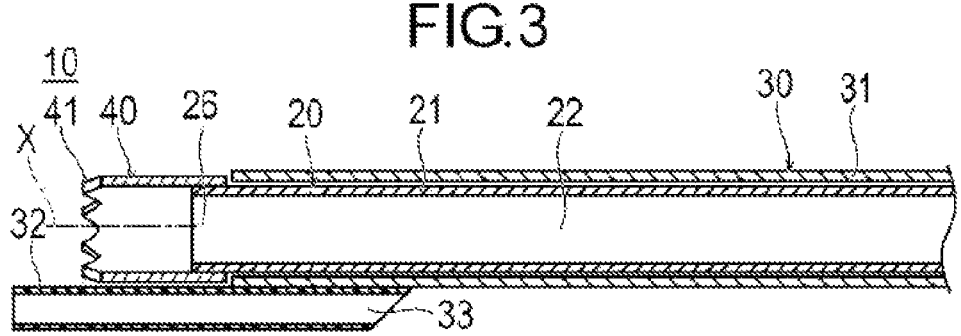
FIG. 3 is a cross-sectional view illustrating a distal portion of the catheter.

As illustrated in FIGS. 1 and 2, the medical device 1 includes a catheter 10 that cuts thrombus and the like, and a drive device 100 that generates a driving force. The catheter 10 is driven by being interlocked with the drive device 100.

As illustrated in FIGS. 1 to 3 and 4A, the catheter 10 includes an elongated drive shaft 20 that is rotationally driven, an outer tube 30 that contains the drive shaft 20, a cutting portion 40 that cuts thrombus and a hub portion 50.

The drive shaft 20 transmits a rotational force to the cutting portion 40. The drive shaft 20 is formed with an aspiration lumen 22 for conveying the cut object to the proximal side. The drive shaft 20 includes an elongated tubular drive tube 21 having an axis X and a connection section 24 fixed to a proximal portion of the drive tube 21.

The drive tube 21 penetrates the outer tube 30, and the cutting portion 40 is fixed to a distal portion of the drive tube 21. The proximal portion of the drive tube 21 is positioned on the inside of the hub portion 50. The drive tube 21 is rotationally driven by a rotary drive shaft 121, which will be described later, via the connection section 24. The drive tube 21 has an inlet portion 26 into which a target to be aspirated (cut thrombus or the like) enters, at a distal end of the drive tube 21. A proximal end of the drive tube 21 has a lumen that is closed and is fixed to the connection section 24. The drive tube 21 has a lead-out unit 25 in which the aspiration lumen 22 is opened, on a side surface of the proximal portion of the drive tube 21 positioned on the inside of the hub portion 50. The lead-out unit 25 is an outlet through which the thrombus that has entered the inside of the drive tube 21 from the inlet portion 26 is discharged.

The drive tube 21 has the characteristics of being flexible and capable of transmitting rotational power from the proximal side to the distal side. The surface of the proximal portion of the drive tube 21 positioned on the inside of the hub portion 50 has a smooth surface texture and high dimensional accuracy. Accordingly, the drive tube 21 can rotate at high speed on the inside of the hub portion 50 while being sealed by a sealing unit 62. The surface of the drive tube 21 may be subjected to plating treatment or polishing treatment so as to have a smooth surface texture.

The drive tube 21 may be configured as one integral member, or may be configured with a plurality of members. For example, the distal portion and the proximal portion of the drive tube 21 may be configured with different members. A part of the drive tube 21 may be, for example, a pipe body in which a plurality of wire rods in a spiral shape are arranged and interlocked with each other. Otherwise, the drive tube 21 may be formed with spiral slits or grooves by laser processing or the like in order to adjust the rigidity along the length thereof depending on the location of the spiral slits or grooves.

As the material of the drive tube 21, for example, stainless steel, polyolefin such as Ta, Ti, Pt, Au, W, polyethylene, and polypropylene, polyester such as polyamide and polyethylene terephthalate, fluorine-based polymer such as ETFE, polyether ether ketone (PEEK), polyimide, and the like can be preferably used. Further, the drive tube 21 may be made of a plurality of materials, and a reinforcing member such as a wire rod may be embedded.

The connection section 24 is a substantially columnar member fixed to the proximal end of the drive tube 21. The connection section 24 is a member that is interlocked with the rotary drive shaft 121 and receives rotational power therefrom. A proximal portion of the connection section 24 includes a concave portion 27 in which the rotary drive shaft 121 is fitted. The connection section 24 seals the lumen at the proximal end of the drive tube 21.

The outer tube 30 includes an outer tube main body 31 that contains the drive shaft 20 so that the drive shaft 20 is rotatable therewithin, and a distal tube 32 that is fixed to a side surface of a distal portion of the outer tube main body 31.

The outer tube main body 31 is a tubular body, and a proximal end is fixed to the hub portion 50. A distal end of the outer tube main body 31 is positioned on the proximal side of the cutting portion 40. The outer tube main body 31 has a bent portion 34 that is bent at a predetermined angle at the distal portion. The bent portion 34 causes a change in the orientation of the distal end of the outer tube main body 31 when the outer tube main body 31 is rotated.

The distal tube 32 is fixed to an outer peripheral surface of the distal portion of the outer tube main body 31. The distal tube 32 has a guide wire lumen 33 into which a guide wire can be inserted.

The material of the outer tube main body 31 and the distal tube 32 is not particularly limited, and for example, polyethylene, polyolefin such as polypropylene, polyester such as polyamide and polyethylene terephthalate, various types of elastomers, fluorine-based polymer such as ETFE, polyether ether ketone (PEEK), polyimide, and the like can be preferably used. Further, the outer tube main body 31 may be made of a plurality of materials, and a reinforcing member such as a wire rod may be embedded.

The cutting portion 40 is a member for cutting thrombus. The cutting portion 40 is fixed to an outer peripheral surface of the distal portion of the drive tube 21. The cutting portion 40 includes a cylindrical body that protrudes toward the distal side of the drive tube 21. A distal end of the cylindrical body of the cutting portion 40 is provided with a sharp blade 41. The shape of the blade 41 is not particularly limited. The cutting portion 40 may have a large number of fine abrasive grains instead of the blade 41.

The material of the cutting portion 40 preferably has strength sufficient to be capable of cutting thrombus, and for example, stainless steel, Ta, Ti, Pt, Au, W, shape memory alloy, or the like can be preferably used. The material of the cutting portion 40 may be a resin such as engineering plastic, e.g., polyether ether ketone (PEEK).

The hub portion 50 includes a hub distal portion 61, the sealing unit 62, a seal fixing portion 65, and a support portion 70. The hub portion 50 further includes a hub intermediate portion 51 and a hub proximal portion 52.

The hub distal portion 61 includes a space portion 63 and an aspiration port 64. The space portion 63 has an internal space 63A through which the drive tube 21 passes and within which the drive tube 21 rotates. The aspiration port 64 can be connected to an aspiration tube 131 of the drive device 100 which will be described later. The aspiration port 64 communicates with the internal space 63A. The hub distal portion 61 is liquid-tightly fixed to a proximal end of the outer tube 30. The proximal portion of the drive tube 21 that penetrates the outer tube 30 is positioned in the internal space 63A. The lead-out unit 25 of the drive tube 21 is positioned in the internal space 63A. Therefore, the negative pressure acting on the aspiration port 64 from the aspiration tube 131 acts on the inside of the drive tube 21 through the lead-out unit 25.

The sealing unit 62 is in contact with the outer peripheral surface of the drive tube 21 on the proximal side of the space portion 63. The sealing unit 62 prevents the escape of the negative pressure in the internal space 63A. Since the sealing unit 62 comes into contact with the drive tube 21 rotating at a high speed, it is preferable that the material of the sealing unit 62 has low friction resistance, high heat resistance, low linear expansion coefficient, and high wear resistance. The material of the sealing unit 62 is, for example, a fluorine-based resin such as ultra-high molecular weight polyethylene, polyester, polyamide, polytetrafluoroethylene, or a combination of two or more thereof (polymer alloy, polymer blend, laminated body and the like).

The seal fixing portion 65 is a tubular member that fixes the sealing unit 62 to the hub distal portion 61. The seal fixing portion 65 faces the internal space 63A from the proximal side of the hub distal portion 61 and is in contact with a surface on the proximal side of the sealing unit 62.

The support portion 70 is a tubular member that fixes the hub distal portion 61 and the hub intermediate portion 51. The support portion 70 is fixed to an outer peripheral surface of the hub distal portion 61 on the proximal side of the hub distal portion 61 and an outer peripheral surface of the hub intermediate portion 51 on the distal side of the hub intermediate portion 51.

The drive tube 21 passes through the hub intermediate portion 51 and is rotatable relative to the hub intermediate portion 51. The hub intermediate portion 51 is fixed to the hub distal portion 61 by the support portion 70.

The hub proximal portion 52 is fixed to the proximal side of the hub intermediate portion 51. The hub proximal portion 52 includes a first engagement portion 53, a second engagement portion 54, an insertion portion 55, and a hub opening portion 56.

The first engagement portion 53 is formed on an outer peripheral surface of the hub proximal portion 52. The shape of an outer peripheral surface of the first engagement portion 53 is a regular polygon centered on the axis X in the cross-section orthogonal to the axis X. The number of corners of the polygon is not limited to any one number. In the present embodiment, the polygon is an octagon. Therefore, the first engagement portion 53 has a plurality of contact surfaces 53A arranged in the circumferential direction. The plurality of contact surfaces 53A are formed in rotational symmetry around the axis X. The contact surface 53A is a surface that comes into contact with an attaching unit 163 which will be described later.

The second engagement portion 54 is a flat surface formed continuously from the first engagement portion 53 on the proximal side of the first engagement portion 53. The second engagement portion 54 is a flat surface that is orthogonal to the axis X and faces the distal side. The second engagement portion 54 extends outward in the radial direction from a proximal end of the first engagement portion 53. In other words, the maximum outer diameter of the second engagement portion 54 is greater than the maximum outer diameter of the first engagement portion 53. The outer edge of the second engagement portion 54 having the maximum outer diameter is a perfect circle centered on the axis X. The second engagement portion 54 is a surface that comes into contact with a movement blocking portion 163B which will be described later.

The insertion portion 55 is a tubular part continuously formed on the proximal side the second engagement portion 54. The insertion portion 55 is inserted into and supported by a hub support portion 111 of the drive device 100 which will be described later. The insertion portion 55 is slidable with respect to the hub support portion 111.

The hub opening portion 56 opens toward the proximal side at a proximal end of the hub proximal portion 52. The hub opening portion 56 contains the connection section 24 therein.

The material of the hub proximal portion 52 is not particularly limited, but at least the insertion portion 55 is preferably formed of a material having low friction resistance. As the material having low friction resistance, for example, polyester such as polyamide and polyethylene terephthalate, fluorine-based polymer such as tetrafluoroethylene-ethylene copolymer (ETFE), polyether ether ketone (PEEK), polyimide, and the like can be preferably used.

Figure 4A:
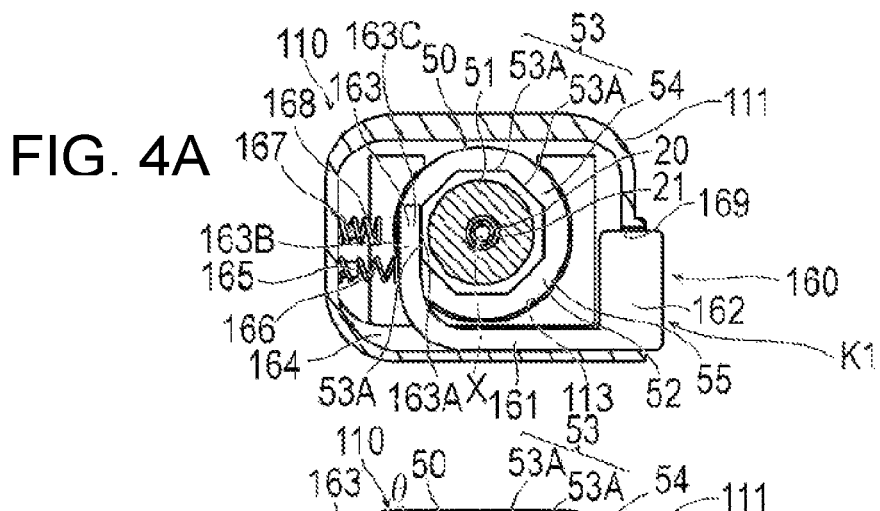
FIGS. 4A-C are cross-sectional views taken along line A-A of FIG. 2.

Next, the drive device 100 will be described. As illustrated in FIGS. 1, 2, and 4A, the drive device 100 includes a casing 110, a drive unit 120 that generates the rotational force, an aspiration unit 130 that generates an aspiration force, a battery 140, and a switch 150.

The drive unit 120 includes the rotary drive shaft 121 and a first motor 122. The rotary drive shaft 121 can be connected to the connection section 24 of the catheter 10. The first motor 122 obtains electric power from the battery 140 to rotate the rotary drive shaft 121. The rotation speed of the first motor 122 is not limited to any one speed, but may be, for example, 5,000 to 200,000 rpm.

The aspiration unit 130 includes the aspiration tube 131, a pump 132, a second motor 133, a waste liquid tube 134, and a waste liquid pack 135. The aspiration tube 131 can be connected to the aspiration port 64 of the catheter 10. The second motor 133 obtains electric power from the battery 140 and drives the pump 132. The pump 132 is driven by the second motor 133 and applies a negative pressure to the aspiration tube 131. Further, the pump 132 discharges the fluid aspirated through the aspiration tube 131 to the waste liquid tube 134. The waste liquid tube 134 is interlocked with the pump 132. The waste liquid tube 134 conveys the waste liquid discharged from the pump 132 to the waste liquid pack 135.

The switch 150 is a part that is operated to start and stop the supply of electric power from the battery 140 to the first motor 122 and the second motor 133. The switch 150 is fixed to the casing 110. Each time the switch 150 is pressed, the supply of electric power is switched on and off.

The casing 110 includes the hub support portion 111 provided at a distal portion of the casing 110 and a containing unit 112 provided at a proximal portion of the casing 110.

The containing unit 112 contains the first motor 122, the second motor 133, the pump 132, the battery 140, and the like. In addition, in the containing unit 112, the switch 150 is fixed so as to be exposed on an outer surface of the containing unit 112 for operation. The aspiration tube 131 and the waste liquid tube 134 are led out from the containing unit 112.

The hub support portion 111 is interlocked with the insertion portion 55 as the insertion portion 55 of the catheter 10 is inserted thereinto. The hub support portion 111 includes a receiving unit 113 and an operation unit 160.

The receiving unit 113 receives and supports an outer peripheral surface of the insertion portion 55 of the hub portion 50. The receiving unit 113 slidably supports the outer peripheral surface of the insertion portion 55. The material of the casing 110 is not particularly limited, but at least the receiving unit 113 is preferably formed of a material having low friction resistance. As the material having low friction resistance is, for example, polyester such as polyamide and polyethylene terephthalate, fluorine-based polymer such as tetrafluoroethylene-ethylene copolymer (ETFE), polyether ether ketone (PEEK), polyimide, and the like can be preferably used. The receiving unit 113 may be provided with a bearing so as to rotatably support the hub portion 50. For example, an outer ring of the bearing may be fixed to the hub support portion 111, and the insertion portion 55 may be inserted into an inner ring of the bearing.

The operation unit 160 is a part for interlocking the catheter 10 to the drive device 100 and detaching the catheter 10 from the drive device 100. As illustrated in FIGS. 2 and 4A, the operation unit 160 includes a moving unit 161 which is moved by an operator, a sliding groove 164 in which the moving unit 161 slides, and a penetrating portion 169 in which a through-hole is formed. The operation unit 160 further includes a first biasing member 166 and a second biasing member 168, that bias the moving unit 161, and a first projection portion 165 and a second projection portion 167 that restrict the positions of the first biasing member 166 and the second biasing member 168, respectively. The first biasing member 166 and the second biasing member 168 are arranged in parallel.

The sliding groove 164 is formed on an inner peripheral surface of the hub support portion 111 in a direction orthogonal to the axis X of the drive tube 21. One end of the sliding groove 164 communicates with the penetrating portion 169 that penetrates from the inner peripheral surface of the hub support portion 111 to an outer peripheral surface thereof. The penetrating portion 169 defines the through-hole. An edge portion 169A on the outer side of the penetrating portion 169 is positioned on the same flat surface. The moving unit 161 is slidably contained through the sliding groove 164. The moving unit 161 includes a pressing unit 162 exposed to the outside from the penetrating portion 169 and the attaching unit 163 attached to the contact surface 53A. An inner edge 163C on the distal side of the attaching unit 163 has an inclined surface such that the thickness of the inner edge 163C narrows in the distal direction. The first projection portion 165 and the second projection portion 167 are formed on the inner peripheral surface of the hub support portion 111 on the side opposite to the side on which the penetrating portion 169 is formed. The first biasing member 166 and the second biasing member 168 are, for example, coil springs. One end of the first biasing member 166 is fitted and fixed to the first projection portion 165. The other end of the first biasing member 166 abuts the attaching unit 163. The first biasing member 166 comes into contact with the attaching unit 163 in a state where the first biasing member 166 is compressed as compared with a natural state where no external force acts. Therefore, the first biasing member 166 biases the attaching unit 163 toward the contact surface 53A of the hub portion 50.

One end of the second biasing member 168 is fitted and fixed to the second projection portion 167. A spring constant of the second biasing member 168 is preferably greater than a spring constant of the first biasing member 166. The spring constant can be appropriately set depending on the wire diameter of the wire rod used, the material, the distance between the pitches of the spiral, and the like. The other end of the second biasing member 168 is positioned to be separated from the attaching unit 163. The other end of the second biasing member 168 can be made to abut the attaching unit 163 by moving the moving unit 161. When the second biasing member 168 abuts the attaching unit 163, the second biasing member 168 biases the attaching unit 163 toward the contact surface 53A of the hub portion 50 (refer to FIG. 4B).

In a state where the hub portion 50 is contained in the hub support portion 111, the attaching unit 163 biased by the first biasing member 166 can be in contact with one of the contact surfaces 53A of the first engagement portion 53. Accordingly, the attaching unit 163 blocks the rotation of the hub portion 50 around the axis X. The surface of the attaching unit 163 that is in contact with the contact surface 53A is a rotation blocking portion 163A that blocks the rotation of the hub portion 50. For example, the rotation blocking portion 163A is the surface of the attaching unit 163 facing a direction that intersects the axis X of the hub portion 50.

In a state where the hub portion 50 is contained in the hub support portion 111, as illustrated in FIG. 2, the surface of the attaching unit 163 on the proximal side of the attaching unit 163 can come into contact with the second engagement portion 54 of the hub portion 50. Accordingly, the attaching unit 163 blocks the movement of the hub portion in the axial direction (which is also the distal direction) such that the hub portion 50 does not come off from the hub support portion 111. The surface of the attaching unit 163 that is in contact with the second engagement portion 54 is the movement blocking portion 163B that blocks the movement of the hub portion 50 in the axial direction. For example, the movement blocking portion 163B is the surface of the attaching unit 163 facing the direction parallel to the axis X of the hub portion 50.

Next, a method of using the medical device 1 according to the first embodiment will be described by taking as an example a case of cutting and aspirating thrombus, calcified lesion and the like in a blood vessel.

First, the operator inserts a guide wire (not illustrated) into the blood vessel and makes the guide wire reach the vicinity of the thrombus. Next, the operator inserts the proximal end of the guide wire into the guide wire lumen 33 of the catheter 10 illustrated in FIGS. 1 and 2. After this, the catheter 10 is maneuvered to reach the vicinity of the thrombus using the guide wire as a guide.

Next, as illustrated in FIG. 2, the operator inserts the insertion portion 55 of the catheter 10 into the hub support portion 111 of the drive device 100. Accordingly, the inner edge 163C of the attaching unit 163 positioned on the hub support portion 111 is pressed to the side by the insertion portion 55. Therefore, the first biasing member 166 and the second biasing member 168 are compressed, as the attaching unit 163 moves to the side. As a result, the insertion portion 55 moves on the inside of the hub support portion 111 toward the proximal side past the attaching unit 163. The insertion portion 55 is supported by the receiving unit 113 to be rotatable relative to the receiving unit 113. At this time, the rotary drive shaft 121 is connected to the connection section 24.

When the insertion portion 55 moves past the attaching unit 163, as illustrated in FIG. 4A, the rotation blocking portion 163A is pressed by the first biasing member 166 and is attached to one of the contact surfaces 53A. Accordingly, the rotation of the hub portion 50 with respect to the drive device 100 is blocked. Furthermore, as illustrated in FIGS. 2 and 4A, the movement blocking portion 163B engages the second engagement portion 54. As a result, the hub portion 50 is prevented from coming off from the drive device 100 in the axial direction. Therefore, the operator can operate the hub portion 50 integrally with the drive device 100. Next, as illustrated in FIG. 2, the operator interlocks the aspiration tube 131 to the aspiration port 64.

Figure 4B:
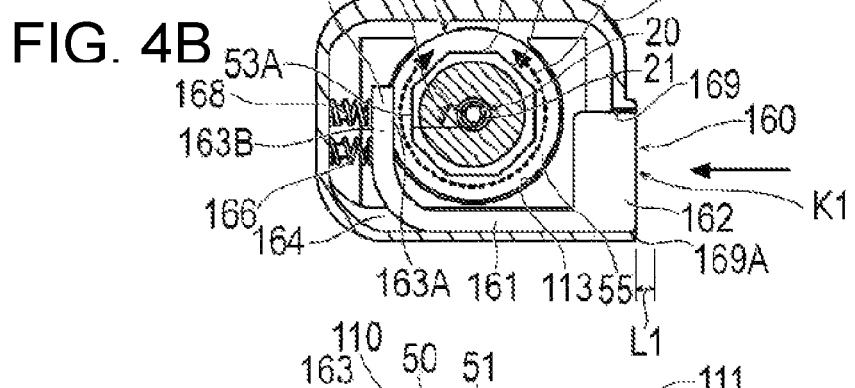

There is a case where the operator desires to rotate the catheter 10 in order to change the position of the cutting portion 40 in the circumferential direction. When the catheter 10 rotates, the direction of the bent portion 34 of the outer tube 30 changes, and the position of the cutting portion 40 can be changed. When rotating the catheter 10, as illustrated in FIG. 4B, the operator presses the pressing unit 162.

When the operator presses the pressing unit 162 in a lateral direction relative to the axis X in a state where the rotation blocking portion 163A is in contact with the contact surface 53A, the moving unit 161 moves through the sliding groove 164. Accordingly, the first biasing member 166 is compressed, and the rotation blocking portion 163A is separated from the contact surface 53A. When the pressing unit 162 moves a first distance L1, the moving unit 161 comes into contact with the second biasing member 168. At this time, the rotation blocking portion 163A is separated from the first engagement portion 53, and the rotation of the hub portion 50 is no longer blocked. Therefore, the pressing unit 162 is referred to herein as a first releasing portion K1 that releases a state in which the hub portion 50 is blocked from rotating. Meanwhile, the movement blocking portion 163B is in contact with the second engagement portion 54. Therefore, the limitation on the movement of the hub portion 50 in the axial direction by the movement blocking portion 163B is maintained. Therefore, the insertion portion 55 becomes rotatable while still being supported by the hub support portion 111.

In order to further move the moving unit 161 in the lateral direction from a state where the moving unit 161 is in contact with the second biasing member 168, it is necessary to compress both the first biasing member 166 and the second biasing member 168. Therefore, the resistance for pressing the pressing unit 162 increases. Furthermore, since the spring constant of the second biasing member 168 is greater than the spring constant of the first biasing member 166, the second biasing member 168 will be more resistant to compression. Therefore, the operator can easily recognize that the moving unit 161 has come into contact with the second biasing member 168. Furthermore, when the moving unit 161 comes into contact with the second biasing member 168, the surface of the pressing unit 162 is aligned with the surface of the penetrating portion 169 on which the edge portion 169A is present. Therefore, it becomes difficult for the operator to press the pressing unit 162. Therefore, it is possible to prevent the hub portion 50 from being unintentionally separated from the drive device 100 in the axial direction if the operator presses the pressing unit 162 with too much force in the lateral direction. Accordingly, the insertion portion 55 can rotate on the inside of the receiving unit 113 while the insertion portion 55 is prevented from being disengaged in the axial direction. At this time, since the insertion portion 55 and the receiving unit 113 are made of a low friction material, the insertion portion 55 and the receiving unit 113 can be easily rotated. The operator can press the pressing unit 62 in the lateral direction with the finger of one hand while holding the outer side of the drive device 100 with the same hand. Accordingly, the operator can rotate the hub portion 50 by one-handed operation, without detaching the hub portion 50 from the drive device 100 in the axial direction. Therefore, the operator can grip the hub portion 50 with the opposite hand and rotate the hub portion 50 in an appropriate direction. As a result, the hub portion 50 can be rotated without rotating the drive device 100, and the rotational force can be effectively transmitted to the bent portion 34. After that, when the operator stops pressing the pressing unit 162, the rotation blocking portion 163A is pressed back by the first biasing member 166 and comes into contact with one of the contact surfaces 53A of the first engagement portion 53. Accordingly, the rotation of the hub portion 50 with respect to the drive device 100 is blocked again. Therefore, the operator can easily change the direction of the bent portion 34 of the outer tube 30 and thus the position of the cutting portion 40, without pulling out the hub portion 50 from the drive device 100. Therefore, the direction of the cutting portion 40 can be easily and effectively changed without rotating the drive device 100.

The first engagement portion 53 includes the plurality of contact surfaces 53A arranged in the circumferential direction. Therefore, the hub portion 50 can attain different angular positions with respect to the drive device 100 as it rotates between the contact surfaces 53A that are adjacent to each other in the circumferential direction by an angle θ. The angle θ is also the rotation angle defined by each of the contact surfaces 53A, which are arranged symmetrically about the center of the hub portion 50. The larger the number of contact surfaces 53A of the first engagement portion 53, the finer the angle of the hub portion 50 with respect to the drive device 100 can be adjusted. On the other hand, the larger the number of contact surfaces 53A of the first engagement portion 53, the smaller the angle in the circumferential direction defined by one contact surface 53A, and weaker the force that limits rotation. Further, the smaller the number of the contact surfaces 53A of the first engagement portion 53, the coarser the adjustment of the angle of the hub portion 50 with respect to the drive device 100. On the other hand, the smaller the number of the contact surfaces 53A of the first engagement portion 53, the greater the angle in the circumferential direction defined by one contact surface 53A, and stronger the force that limits rotation.

Figure 4C:
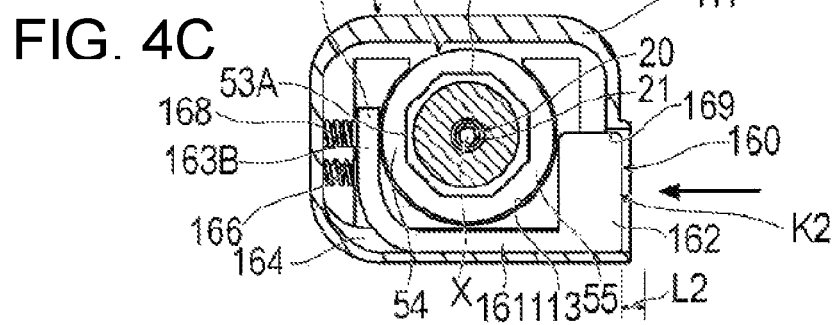

When the pressing unit 162 is further pressed in the lateral direction in a state where the moving unit 161 is in contact with the second biasing member 168 (the state illustrated in FIG. 4B), the moving unit 161 moves through the sliding groove 164 as illustrated in FIG. 4C. Then, the first biasing member 166 and the second biasing member 168 are further compressed. When the pressing unit 162 moves a second distance L2 from its initial position (position before being pressed), the movement blocking portion 163B moves from the position on the distal side of the second engagement portion 54 and reaches the position where the movement blocking portion 163B is not in contact with the second engagement portion 54. Note that the second distance L2 is greater than the first distance L1. Accordingly, the limitation on the movement of the hub portion 50 in the axial direction by the movement blocking portion 163B. Therefore, the operator can pull out the hub portion 50 from the hub support portion 111 to the distal side. Therefore, the pressing unit 162 is also referred to herein as a second releasing portion K2 that releases a state in which the hub portion 50 is blocked from movement in the axial direction. The operator can change the catheter 10 or the drive device 100 or adjust the position by pulling out the hub portion 50 from the drive device 100. The disconnected hub portion 50 and drive device 100 can be interlocked with each other again.

Next, the operator presses the switch 150 in a state where the hub portion 50 is interlocked with the drive device 100 (refer to FIG. 1). As a result, electric power is supplied from the battery 140 to the first motor 122 and the second motor 133. The first motor 122 rotates the rotary drive shaft 121 and rotates the connection section 24 connected to the rotary drive shaft 121. Accordingly, the drive shaft 20 rotates and the cutting portion 40 rotates. The rotating cutting portion 40 cuts the thrombus in the blood vessel.

The second motor 133 actuates the pump 132. Accordingly, as illustrated in FIG. 2, a negative pressure acts on the internal space 63A via the aspiration tube 131. Therefore, a negative pressure acts on the aspiration lumen 22 of the drive tube 21 from the lead-out unit 25 positioned in the internal space 63A. Therefore, the thrombus cut by the blade 41 of the cutting portion 40 passes through the inner side of the cutting portion 40 and is aspirated into the aspiration lumen 22 from the inlet portion 26 of the drive tube 21.

The aspirated thrombus reaches the pump 132 through the lead-out unit 25, the internal space 63A, and the aspiration tube 131. As illustrated in FIG. 1, the thrombus that has reached the pump 132 is discharged to the waste liquid pack 135 via the waste liquid tube 134. After the cutting and aspiration of the thrombus are completed, the operator presses the switch 150. As a result, the supply of electric power from the battery 140 to the first motor 122 and the second motor 133 is stopped. Therefore, the rotation of the drive shaft 20 is stopped and the pump 132 is stopped. Accordingly, the cutting by the cutting portion 40 and the aspiration by the drive tube 21 are stopped. After this, the catheter 10 is drawn out from the blood vessel, and the procedure is completed.

As described above, the medical device 1 according to the first embodiment which is the medical device 1 for cutting and removing an object in the body lumen, includes: the catheter 10 inserted into the body lumen; and the drive device 100 interlocked with the catheter 10. The catheter 10 includes the rotatable drive shaft 20, the outer tube 30 containing the drive shaft 20 so as to be rotatable with respect to the outer tube 30, the cutting portion 40 fixed to a distal portion of the drive shaft 20 to cut the object, and the hub portion 50 fixed to a proximal portion of the outer tube 30 and containing the drive shaft 20 so as to be rotatable with respect to the hub portion 50. The drive device 100 includes the drive unit 120 interlocked with the drive shaft 20 to transmit the rotational force, and the hub support portion 111 with which the hub portion 50 is interlocked. The hub portion 50 has the first engagement portion 53 and the second engagement portion 54 interlocked with the hub support portion 111. The hub support portion 111 includes the rotation blocking portion 163A that is engaged with the first engagement portion 53 to block the rotation of the hub portion 50, the movement blocking portion 163B that is engaged with the second engagement portion 54 to block the movement of the hub portion 50 in the axial direction, and the first releasing portion K1 that releases a state in which the hub portion 50 is blocked from rotating while maintaining a state in which the hub portion 50 is blocked from moving in the axial direction.

In the medical device 1 configured as described above, the hub portion 50 can be rotatable with respect to the drive device 100 while the hub portion 50 is fixed to the drive device 100 in the axial direction by actuating the first releasing portion K1. Therefore, the position of the catheter 10 in the body lumen can be easily changed by rotating the catheter 10 without pulling out the hub portion 50 from the drive device 100. As a result, on the distal side of the drive device 100, the hub portion 50 can be rotated without rotating the drive device 100, and the rotational force can be effectively transmitted to the bent portion 34.

In addition, the first engagement portion 53 has the plurality of contact surfaces 53A arranged in the circumferential direction, and the rotation blocking portion 163A is capable of coming into contact with each of the contact surfaces 53A, the rotation blocking portion 163A blocks the rotation of the hub portion 50 by coming into contact with the contact surface 53A, and the first releasing portion K1 is actuated to separate the rotation blocking portion 163A from the contact surface 53A and make the hub portion 50 rotatable with respect to the rotation blocking portion 163A. Accordingly, the rotation blocking portion 163A can be brought into contact with any one of the contact surfaces 53A arranged in the circumferential direction, and thereby the rotation of the hub portion 50 can be blocked. Therefore, in the medical device 1, the hub portion 50 can be easily interlocked with the drive device 100 at various positions in the rotation direction, and operability and usability are improved. Further, since the first engagement portion 53 is polygonal, the structure is simple and the manufacturing is easy.

In addition, the drive device 100 includes the second releasing portion K2 that releases a state in which the hub portion 50 is blocked from moving in the axial direction, by moving the movement blocking portion 163B from the position on the distal side of the second engagement portion 54. Accordingly, in the medical device 1, the hub portion 50 can be easily detached from the drive device 100 in the axial direction by actuating the second releasing portion K2.

In addition, the drive device 100 has the moving unit 161 that is movable in the direction intersecting with the axis X of the drive shaft 20. The moving unit 161 has the pressing unit 162 exposed to the outside and to be pressed, the rotation blocking portion 163A, and the movement blocking portion 163B. The pressing unit 162 functions as the first releasing portion K1 that separates the rotation blocking portion 163A from the contact surface 53A by being pressed to move the first distance L1, and the pressing unit 162 functions as the second releasing portion K2 that moves the movement blocking portion 163B from the position on the distal side of the second engagement portion 54 by being pressed to move the second distance L2 longer than the first distance L1. Therefore, the medical device 1 can sequentially actuate both the first releasing portion K1 and the second releasing portion K2 by changing the pressing amount of the pressing unit 162. Accordingly, the medical device 1 can release the blocking of rotation and movement of the hub portion 50 by operating only one pressing unit 162 with one hand, so that the operability and usability are improved.

In addition, the drive device 100 includes the biasing member (first biasing member 166 and the second biasing member 168) that biases the moving unit 161, and the biasing force of the first biasing member 166 and the second biasing member 168 when actuating the second releasing portion K2 is greater than the biasing force of the first biasing member 166 when actuating the first releasing portion K1. Accordingly, it is more difficult to actuate the second releasing portion K2 than the first releasing portion K1. Therefore, by actuating only the first releasing portion K1 without actuating the second releasing portion K2, and without detaching the hub portion 50 from the drive device 100 in the axial direction, it becomes easy to adjust the orientation of the catheter 10 with respect to the drive device 100.

In addition, the drive device 100 has the penetrating portion 169 that defines a hole through which the pressing unit 162 is exposed. The pressing unit 162, before being pressed, protrudes outward from the surface on which the edge portion 169A of the hole of the penetrating portion 169 is positioned, and the pressing unit 162, when pressed to move a distance exceeding the first distance L1, is positioned on the inner side of the surface on which the edge portion 169A of the hole of the penetrating portion 169 is positioned. Accordingly, when the pressing unit 162 moves more than the first distance L1, it becomes difficult to press the pressing unit 162. Therefore, it is difficult for the operator to further press the pressing unit 162 and actuate the second releasing portion K2 after pressing the pressing unit 162 and actuating the first releasing portion K1. Accordingly, it is possible to prevent the hub portion 50 from being unintentionally separated from the drive device 100 in the axial direction if the operator presses the pressing unit 162 with too much force.

Second Embodiment

Figure 5A:
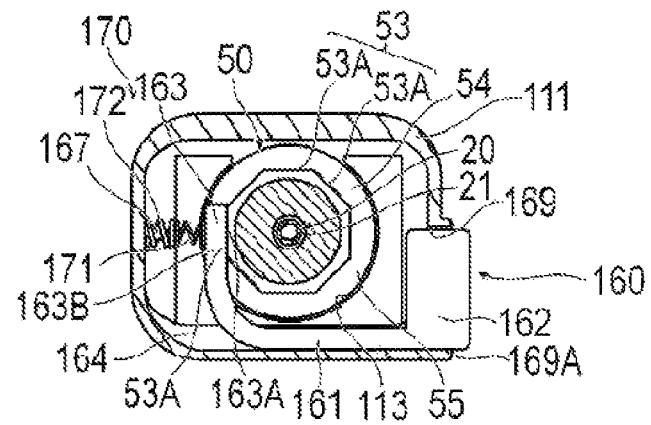
FIGS. 5A-5C are cross-sectional views illustrating a medical device according to a second embodiment.
Figure 5B:
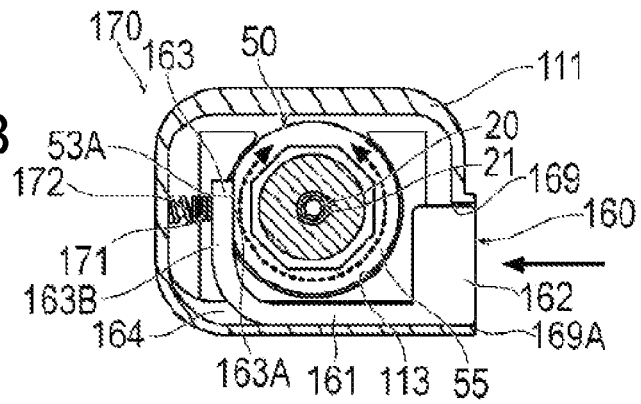
Figure 5C:
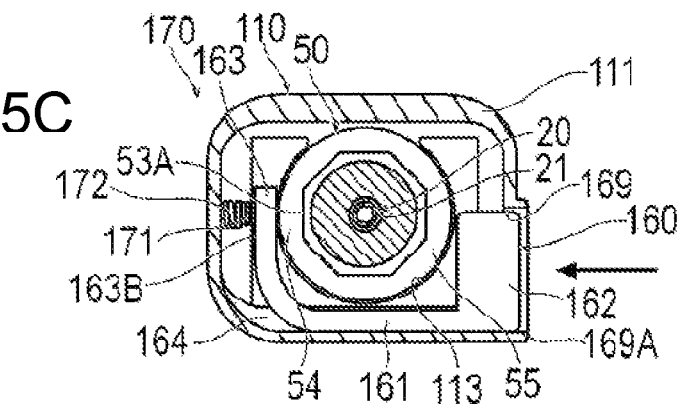

As illustrated in FIGS. 5A-5C, a medical device according to a second embodiment is different from the medical device 1 according to the first embodiment in that a first biasing member 171 and a second biasing member 172 of the drive device 100 are interlocked with each other in series. The parts having the same functions as those in the first embodiment will be given the same reference numerals, and the description thereof will not be repeated.

In the second embodiment, as illustrated in FIG. 5A, the first biasing member 171 and the second biasing member 172 are interlocked with each other in series. The first biasing member 171 having a low spring constant comes into contact with the attaching unit 163, and the second biasing member 172 having a high spring constant is interlocked with the inner peripheral surface of the hub support portion 111. Note that the first biasing member 171 and the second biasing member 172 may be arranged in reverse.

In a state where the hub portion 50 is contained in the hub support portion 111, the rotation blocking portion 163A is in contact with one of the contact surfaces 53A by the biasing force of the first biasing member 171 and the second biasing member 172. Further, the movement blocking portion 163B is engaged with the second engagement portion 54. Therefore, the rotation of the hub portion 50 is blocked by the rotation blocking portion 163A, and the movement of the hub portion 50 in the axial direction is blocked by the movement blocking portion 163B.

When the operator presses the pressing unit 162 in a state where the rotation blocking portion 163A is in contact with the contact surface 53A, as illustrated in FIG. 5B, the first biasing member 171 having a low spring constant is mainly compressed. At this time, the second biasing member 172 having a high spring constant does not compress as much as the first biasing member 171. Accordingly, the rotation blocking portion 163A is separated from the contact surface 53A. When the moving unit 161 moves a predetermined distance, the first biasing member 171 is compressed almost completely. Therefore, when the operator further presses the pressing unit 162, the second biasing member 172 having a high spring constant is mainly compressed. Therefore, the operator can easily recognize that the first biasing member 171 has been compressed completely. At this time, the rotation blocking portion 163A is separated from the first engagement portion 53, and the rotation of the hub portion 50 is no longer blocked, while the movement blocking portion 163B is in contact with the second engagement portion 54. Therefore, the limitation on the movement of the hub portion 50 in the axial direction by the movement blocking portion 163B is maintained. Accordingly, the operator can rotate the hub portion 50 without detaching the hub portion 50 from the drive device 100 in the axial direction.

When the operator further presses the pressing unit 162, as illustrated in FIG. 5C, the second biasing member 172 is compressed. Then, the moving unit 161 moves through the sliding groove 164. When the movement blocking portion 163B reaches the position where the movement blocking portion 163B is not in contact with the second engagement portion 54, the movement of the hub portion 50 in the axial direction is no longer blocked by the movement blocking portion 163B. At that time, the operator can pull out the hub portion 50 from the hub support portion 111 to the distal side.

Third Embodiment

As illustrated in FIGS. 6 to 8A-8B, a medical device according to a third embodiment is different from the medical device 1 according to the first embodiment in the structure of a movement blocking portion 185 and a second engagement portion 180. Note that the parts having the same functions as those in the first embodiment will be given the same reference numerals, and the description thereof will not be repeated.

Figure 6:
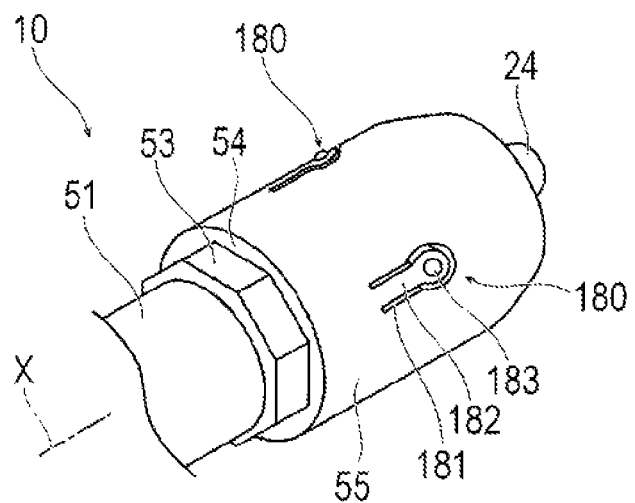
FIG. 6 is a perspective view illustrating a proximal portion of a catheter of a medical device according to a third embodiment.
Figure 7:
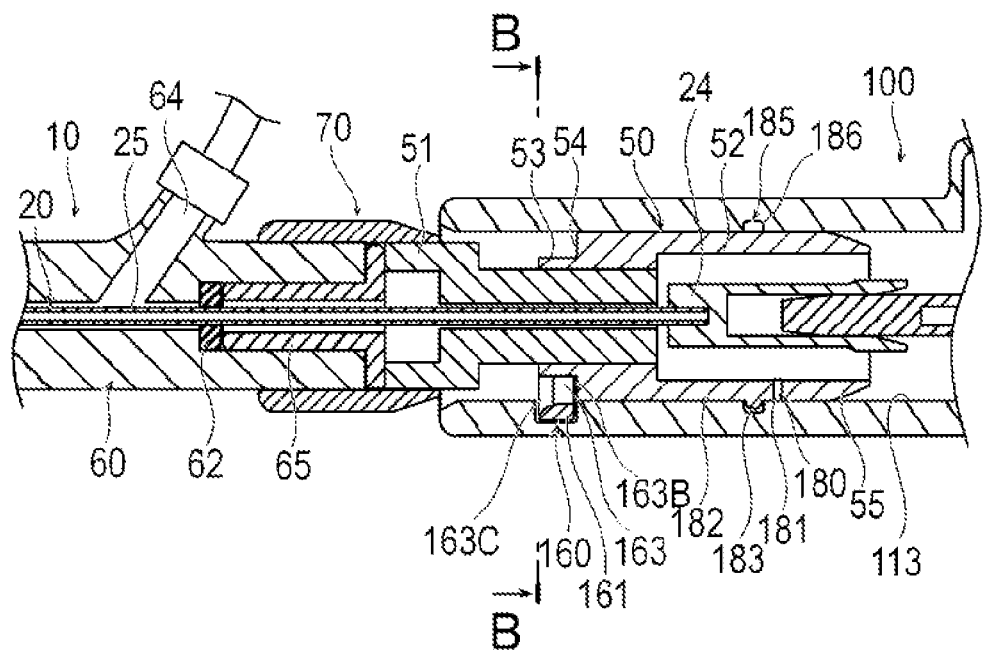
FIG. 7 is a cross-sectional view illustrating a proximal portion of the medical device according to the third embodiment.

In the third embodiment, as illustrated in FIGS. 6 and 7, the insertion portion 55 of the catheter 10 has at least one second engagement portion 180. The second engagement portion 180 includes a U-shaped cut portion 181, a beam portion 182 that is a cantilever beam surrounded by the cut portion 181, and a convex portion 183 that protrudes outward in the radial direction from an end portion of the beam portion 182.

The receiving unit 113 of the drive device 100 is formed with the movement blocking portion 185. The movement blocking portion 185 has a groove portion 186 formed on an inner peripheral surface of the receiving unit 113. The groove portion 186 extends in the circumferential direction on the inner peripheral surface of the receiving unit 113.

Unlike the first embodiment, the drive device 100 is not provided with the second biasing member 168 and the second projection portion 167 (refer to FIG. 4A).

When the insertion portion 55 is inserted into the receiving unit 113, the beam portion 182 bends and the convex portion 183 moves to the inner side of the insertion portion 55. When the convex portion 183 reaches the groove portion 186 of the receiving unit 113, as illustrated in FIG. 7, the bent portion of the beam portion 182 straightens out and the convex portion 183 becomes lodged in the groove portion 186. Accordingly, the movement blocking portion 185 blocks the movement of the second engagement portion 180 in the axial direction. Since the second engagement portion 180 and the movement blocking portion 185 are a part of the insertion portion 55 and the receiving unit 113, respectively, the second engagement portion 180 and the movement blocking portion 185 are made of a low friction material. Therefore, when the insertion portion 55 is inserted into the receiving unit 113, the convex portion 183 can smoothly move along an inner surface of the receiving unit 113. The convex portion 183 can move on the inside of the groove portion 186 in the circumferential direction.

Figure 8A:
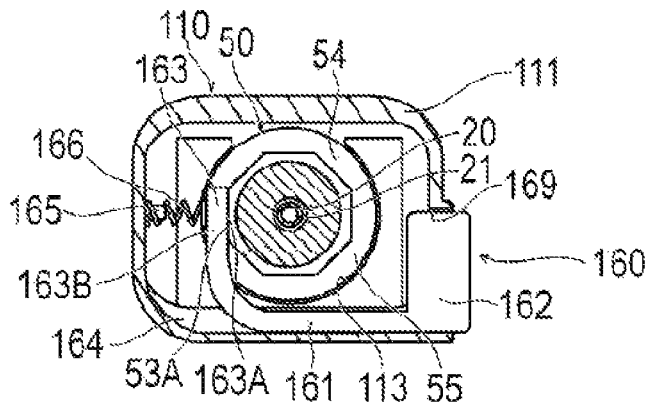
FIGS. 8A-8B are cross-sectional views taken along line B-B of FIG. 7.

In a state where the hub portion 50 is contained in the hub support portion 111, as illustrated in FIG. 8A, the rotation blocking portion 163A is in contact with one of the contact surfaces 53A by the biasing force of the first biasing member 166. Note that, since the second engagement portion 180 and the movement blocking portion 185 block the movement of the hub portion 50 in the axial direction, the attaching unit 163 does not need to block the movement of the hub portion 50 in the axial direction. Therefore, in the third embodiment, the second biasing member 168 (refer to FIGS. 4A-4C) is not provided. The rotation of the hub portion 50 is blocked by the rotation blocking portion 163A, and the movement of the hub portion 50 in the axial direction is blocked by the movement blocking portion 185.

Figure 8B:
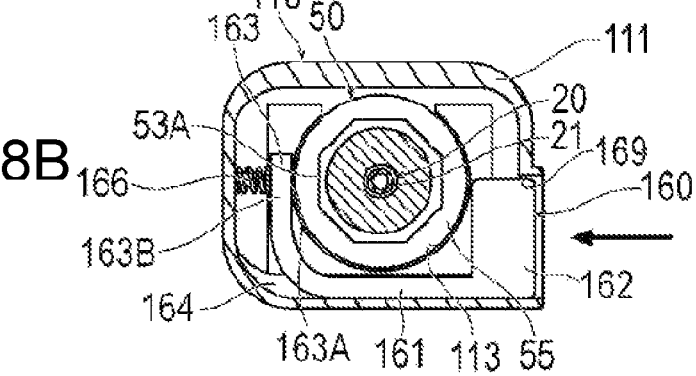

When the operator presses the pressing unit 162 in a state where the rotation blocking portion 163A is in contact with the contact surface 53A, as illustrated in FIG. 8B, the first biasing member 166 is compressed. Accordingly, the rotation blocking portion 163A is separated from the contact surface 53A. Therefore, the rotation of the hub portion 50 is no longer blocked. Meanwhile, as illustrated in FIG. 7, the convex portion 183 of the second engagement portion 180 is contained in the groove portion 186 of the movement blocking portion 185. Therefore, the limitation on the movement of the hub portion 50 in the axial direction by the movement blocking portion 163B is maintained. The convex portion 183 is permitted move inside the groove portion 186 in the circumferential direction. Accordingly, the operator can rotate the hub portion 50 without detaching the hub portion 50 from the drive device 100 in the axial direction.

In a case where the operator desires to detach the hub portion 50 from the drive device 100, the operator pulls the hub portion 50 to the distal side from the drive device 100. When the pulling force is strong enough, the beam portion 182 is deformed and the convex portion 183 is detached from the groove portion 186. The convex portion 183 is able to smoothly move along the inner surface of the receiving unit 113. Accordingly, the operator can pull out the hub portion 50 from the drive device 100 to the distal side.

The drive device 100 may be provided with the second biasing member 168 and the second projection portion 167.

The drive device 100 may include both the movement blocking portion 185 and the movement blocking portion 163B (refer to FIG. 2) similar to that of the first embodiment, as means for limiting the movement of the catheter 10 in the axial direction.

Fourth Embodiment

Figure 9A:
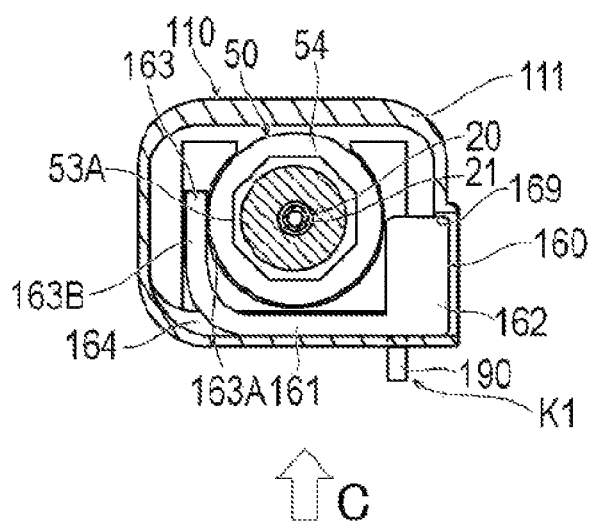
FIGS. 9A-9B are views illustrating a state where a catheter of a medical device according to a fourth embodiment is attachable to and detachable from the drive device.
Figure 9B:
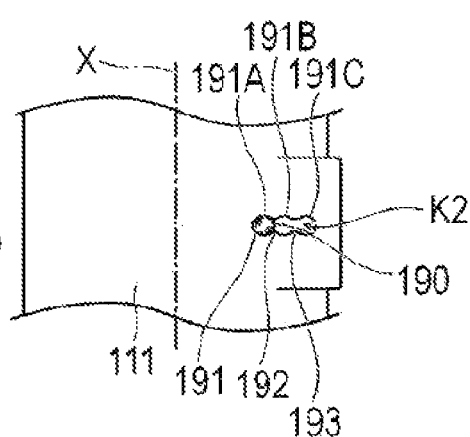

As illustrated in FIGS. 9A-9B, a medical device according to a fourth embodiment is different from the medical device 1 according to the first embodiment in that the drive device 100 is provided with a convex portion 190. The parts having the same functions as those in the first embodiment will be given the same reference numerals, and the description thereof will not be repeated.

In the fourth embodiment, the pressing unit 162 has the convex portion 190 that protrudes in a direction orthogonal to the moving direction of the moving unit 161 and orthogonal to the axis X. The convex portion 190 has a columnar shape. The convex portion 190 penetrates the hub support portion 111 and protrudes outward from an outer surface of the hub support portion 111. The convex portion 190 which is a part of the pressing unit 162 functions as the first releasing portion K1 and the second releasing portion K2. The first releasing portion K1 releases a state in which the hub portion 50 is blocked from rotating. The second releasing portion K2 releases a state in which the movement of the hub portion 50 in the axial direction is blocked.

The hub support portion 111 is formed with an opening portion 191 through which the convex portion 190 penetrates. The opening portion 191 extends along the moving direction of the moving unit 161. The opening portion 191 contains the convex portion 190 and the convex portion 190 is movable while contained in the opening portion 191. The opening portion 191 includes a first opening portion 191A, a second opening portion 191B, and a third opening portion 191C. The first opening portion 191A is farthest from the pressing unit 162. The third opening portion 191C is closest to the pressing unit 162. The second opening portion 191B is positioned between the first opening portion 191A and the third opening portion 191C. The opening portion 191 has a first maintaining unit 192 and a second maintaining unit 193 which are formed at an edge portion along the moving direction. The widths of the openings of the first maintaining unit 192 and the second maintaining unit 193 are slightly smaller than the diameter of the convex portion 190. The width of the opening of the first maintaining unit 192 is preferably smaller than the width of the opening of the second maintaining unit 193, but is not limited thereto. The first maintaining unit 192 is positioned between the first opening portion 191A and the second opening portion 191B. The second maintaining unit 193 is positioned between the second opening portion 191B and the third opening portion 191C.

In the fourth embodiment, a biasing member that biases the moving unit 161 is not provided.

In a state where the operator presses the pressing unit 162 with a large force, the convex portion 190 is positioned at the first opening portion 191A at an end portion of the opening portion 191. The convex portion 190 is maintained at a constant position by the first maintaining unit 192. In this state, the operator can insert the hub portion 50 into the hub support portion 111 without being obstructed by the attaching unit 163. Further, the operator can also pull out the hub portion 50 from the hub support portion 111 without being obstructed by the attaching unit 163.

Figure 10A:
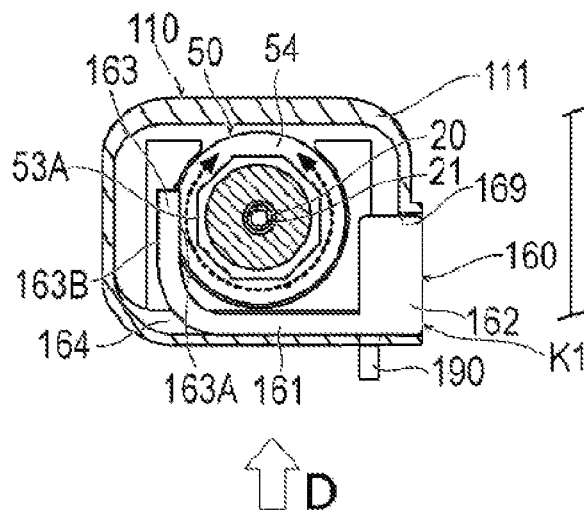
FIGS. 10A-10B are views illustrating a state where the catheter of the medical device according to the fourth embodiment is rotatably interlocked with the drive device.
Figure 10B:
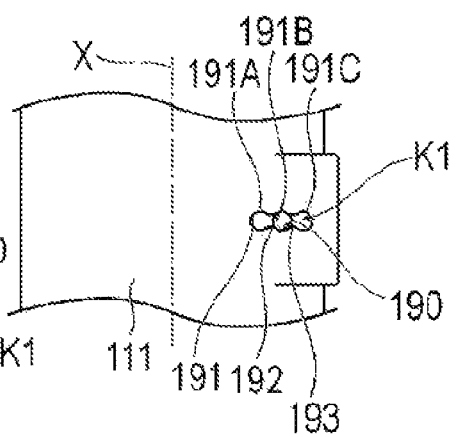

The operator can move the convex portion 190 by operating the convex portion 190 with a finger. When the operator presses the convex portion 190 toward the second opening portion 191B, as illustrated in FIG. 10B, the convex portion 190 overcomes the first maintaining unit 192 while elastically deforming the first maintaining unit 192 and moves to the second opening portion 191B. When the convex portion 190 reaches the second opening portion 191B, the convex portion 190 is sandwiched between the first maintaining unit 192 and the second maintaining unit 193 and is maintained at a constant position. In this state, the movement blocking portion 163B is attached to the second engagement portion 54. Therefore, the movement of the hub portion 50 in the axial direction is blocked by the movement blocking portion 163B. Meanwhile, the rotation blocking portion 163A is separated from the contact surface 53A. Accordingly, the operator can rotate the hub portion 50 without detaching the hub portion 50 from the drive device 100 in the axial direction.

Figure 11A:
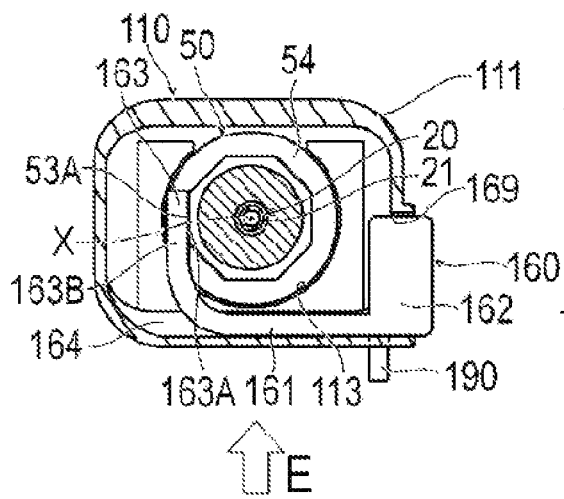
FIGS. 11A-11B are views illustrating a state where the catheter of the medical device according to the fourth embodiment is fixed to the drive device.
Figure 11B:
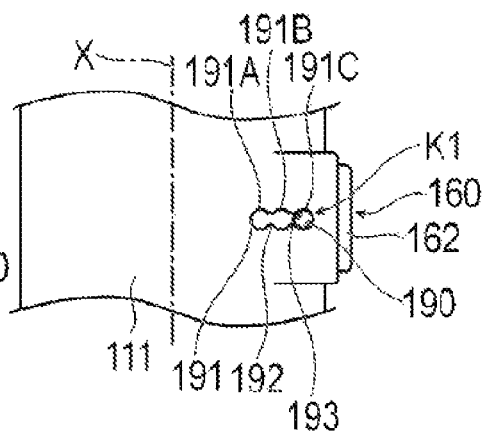

When the operator strongly presses the convex portion 190 toward the third opening portion 191C, as illustrated in FIG. 11B, the convex portion 190 overcomes the second maintaining unit 193 while elastically deforming the second maintaining unit 193 and moves to the third opening portion 191C. When the convex portion 190 reaches the third opening portion 191C, the second maintaining unit 193 maintains the convex portion 190 at a constant position. In this state, the rotation blocking portion 163A is in contact with one of the contact surfaces 53A. Accordingly, the rotation of the hub portion 50 is blocked by the rotation blocking portion 163A. Further, the movement blocking portion 163B is engaged with the second engagement portion 54. Therefore, the movement of the hub portion 50 in the axial direction is blocked by the movement blocking portion 163B. Therefore, the operator can operate the hub portion 50 integrally with the drive device 100.

In a case where the operator desires to rotate the hub portion 50 without detaching the hub portion 50 from the drive device 100, the operator presses the convex portion 190 toward the second opening portion 191B. Accordingly, as illustrated in FIG. 10B, the convex portion 190 overcomes the second maintaining unit 193 while elastically deforming the second maintaining unit 193 and moves to the second opening portion 191B. When the convex portion 190 reaches the second opening portion 191B, the convex portion 190 is sandwiched between the first maintaining unit 192 and the second maintaining unit 193 and is maintained at a constant position. At this time, the width of the opening of the first maintaining unit 192 is smaller than the width of the opening of the second maintaining unit 193. Accordingly, it is possible to prevent the convex portion 190 from exceeding the first maintaining unit 192, as illustrated in FIG. 9B, due to the momentum from the force needed to overcome the second maintaining unit 193. Therefore, it is possible to prevent the hub portion 50 from being unintentionally separated from the drive device 100.

As described above, the drive device 100 according to the fourth embodiment includes the first maintaining unit 192 and the second maintaining unit 193 that are in contact with the moving unit 161 and restrict the movement of the moving unit 161, and the first maintaining unit 192 and the second maintaining unit 193 maintain a state where the first releasing portion K1 and the second releasing portion K2 are actuated. In other words, the first maintaining unit 192 and the second maintaining unit 193 can maintain a state where the rotation blocking portion 163A is separated from the first engagement portion 53 by coming into contact with the moving unit 161 (refer to FIGS. 9A-9B and 10A-10B). Furthermore, the first maintaining unit 192 can maintain a state where the movement blocking portion 163B is separated from the second engagement portion 54 by coming into contact with the moving unit 161 (refer to FIG. 9A). Accordingly, the operator does not need to continue pressing to maintain the actuating state after initial pressing and moving the convex portion 190 and actuating the first releasing portion K1 or the second releasing portion K2. Therefore, the hand used for actuating the first releasing portion K1 or the second releasing portion K2 can be separated from the drive device 100, and the operability is improved. Therefore, for example, the catheter 10 can also be rotated by the hand that has actuated the first releasing portion K1 or the second releasing portion K2, that is, the hand for pressing the convex portion 190.

The present invention also provides a procedure method (treatment method) of cutting and removing the object in the body lumen. The procedure method includes: (1) a step of holding the aforementioned catheter 10 by one hand, holding the drive device 100 by the other hand, inserting the catheter 10 into the body, and advancing to a target site; (2) a step of pressing the convex portion 190 to release the blocking of rotation by the rotation blocking portion 163A, separating the hand that holds the drive device 100 from the drive device 100 in a state where the movement blocking portion 163B continues to block movement in an axial direction, and moving the catheter 10; (3) a step of changing and fixing the position of the cutting portion 40 in the circumferential direction by rotating the catheter 10 in the circumferential direction toward the target site by one hand, and cutting the object by the cutting portion 40 by continuing to press the catheter 10 by the other hand; (4) a step of pressing the convex portion 190 after the cutting is completed, and blocking the rotation of the hub portion 50 by the rotation blocking portion 163A; (5) a step of drawing out the catheter 10 from the body; and (6) a step of releasing the movement blocking portion 163B and the rotation blocking portion 163A using the first releasing portion K1 and the second releasing portion K2, and disconnecting the catheter 10 and the drive device 100. Accordingly, after making it possible for the catheter 10 to rotate with respect to the drive device 100, the catheter 10 can be operated with both hands while maintaining the rotatable state. At this time, both hands can grip and operate the outer tube 30 in the vicinity of the insertion position of the catheter 10 into the body. Accordingly, rather than gripping and operating the hub portion 50, the catheter 10 can be operated near the insertion position into the living body, and torque or force in the axial direction can be easily transmitted to the distal side. Therefore, the object can be cut by moving the catheter 10 in the axial direction while effectively rotating the catheter 10 and directing the cutting portion 40 in a desired direction.

The present invention is not limited to the above-described embodiments, and various modifications are possible by those skilled in the art within the technical idea of the present invention. For example, the body lumen into which the catheter 10 is inserted is not limited to a blood vessel, and may be, for example, a vessel, a ureter, a bile duct, a fallopian tube, a hepatic duct, or the like. Therefore, the object to be cut need not be thrombus.

Further, the lead-out unit that generates the aspiration force of the drive shaft 20 may be formed at a proximal end instead of the side surface of the drive shaft 20. In this case, the drive source (motor or the like) of the drive shaft 20 may be positioned on the side surface side of the drive shaft 20 instead of the proximal side. For example, the drive shaft 20 can receive a rotational driving force from the side surface side via a gear by installing the gear on an outer peripheral surface.

Figure 12:
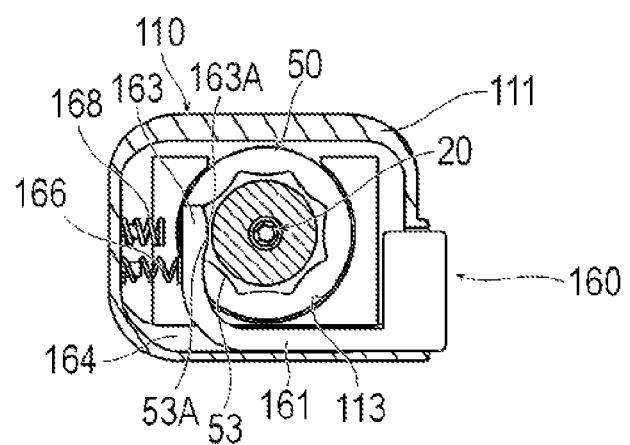
FIG. 12 is a cross-sectional view illustrating a proximal portion of a medical device according to a fifth embodiment.

In addition, the contact surface 53A of the first engagement portion 53 need not be a flat surface as long as it is possible to come into contact with the rotation blocking portion 163A and limit the rotation of the hub portion 50. For example, similar to the modification example illustrated in FIG. 12, the contact surface 53A may be a concave surface. Then, the rotation blocking portion 163A is formed in a projection shape so as to be in close contact with the recessed contact surface 53A. In this case, the rotation blocking portion 163A enters the recessed contact surface 53A when coming into contact with the contact surface 53A. Accordingly, the rotation blocking portion 163A and the contact surface 53A can be firmly engaged with each other. Therefore, the rotation blocking portion 163A can more reliably block the rotation of the hub portion 50.

Further, the rotation blocking portion 163A attached to the contact surface 53A may come into contact not with one contact surface 53A but with two or more contact surfaces 53A at the same time.

What is claimed is:

1. A medical device for cutting an object in a body lumen, comprising:
    a catheter to be inserted into the body lumen; and
    a drive device interlocked with the catheter,
    wherein the catheter includes
        a rotatable drive shaft,
        an outer tube in which the drive shaft is contained so as to be rotatable with respect thereto,
        a cutting portion for cutting the object, fixed to a distal portion of the drive shaft, and
        a hub portion fixed to a proximal portion of the outer tube and in which the drive shaft is contained so as to be rotatable with respect thereto,
    wherein the drive device includes
        a drive unit interlocked with the drive shaft to transmit a rotational force to the drive shaft, and
        a hub support portion with which the hub portion is interlocked,
    wherein the hub portion has first and second engagement portions interlocked with the hub support portion, and
    wherein the hub support portion includes
        a rotation blocking portion that is engaged with the first engagement portion to block the hub portion from rotating with respect to the hub support portion,
        a movement blocking portion that is engaged with the second engagement portion to block movement of the hub portion with respect to the hub support portion in an axial direction, and
        a releasing portion to be actuated to release a state in which a rotation of the hub portion is blocked while maintaining a state in which movement of the hub portion in the axial direction is blocked.

2. The medical device according to claim 1,
    wherein the first engagement portion has a plurality of contact surfaces arranged in a circumferential direction, and the rotation blocking portion is capable of coming into contact with each of the contact surfaces,
    wherein the rotation blocking portion limits rotation of the hub portion by coming into contact with one of the contact surfaces, and
    wherein the releasing portion is actuated to separate the rotation blocking portion from the one contact surface.

3. The medical device according to claim 1,
    wherein the releasing portion is further actuated to release a state in which the movement of the hub portion in the axial direction is blocked, by disengaging the movement blocking portion from the second engagement portion.

4. The medical device according to claim 3,
    wherein the releasing portion includes a slider exposed to the outside, the releasing portion being actuated when the slider is pressed in a direction intersecting with an axis of the drive shaft,
    wherein the slider is actuated to separate the rotation blocking portion from one contact surface of the first engagement portion when the slider is pressed to move a first distance, and
    wherein the slider is further actuated to disengage the movement blocking portion from the second engagement portion when the slider is pressed to move a second distance greater than the first distance.

5. The medical device according to claim 4,
    wherein the drive device includes a biasing member that applies a biasing force to the slider, and
    wherein the biasing force of the biasing member, when the slider is actuated to disengage the movement blocking portion from the second engagement portion, is greater than the biasing force of the biasing member, when the slider is actuated to separate the rotation blocking portion from the one contact surface.

6. The medical device according to claim 5,
    wherein the drive device has a penetrating portion that defines a hole through which the slider is exposed,
    wherein, when the slider is pressed to have a moving distance that is less than the first distance, the slider protrudes outwardly from a surface on which an edge portion of the hole of the penetrating portion is positioned, and
    wherein, when the slider is pressed to have a moving distance exceeding the first distance, the slider is positioned on an inner side of the surface on which the edge portion of the hole of the penetrating portion is positioned.

7. The medical device according to claim 6,
    wherein the drive device includes a maintaining unit that comes into contact with the slider and maintains a position of the slider, and
    wherein the maintaining unit can maintain the position of the slider in a state where the slider has moved by at least one of the first distance and the second distance.

8. A medical device for cutting an object in a body lumen, comprising:
    a catheter to be inserted into the body lumen, the catheter including a rotatable drive shaft, a cutting portion for cutting the object, fixed to a distal portion of the drive shaft, and an outer tube extending in an axial direction of the drive shaft and surrounding the drive shaft; and
    a drive device including a drive unit interlocked with the drive shaft to transmit a rotational force to the drive shaft,
    wherein the catheter further includes a hub portion fixed to a proximal end of the outer tube, the hub portion being rotatable with the outer tube and including a plurality of contact surfaces around a rotational axis thereof, and
    wherein the drive device further includes a hub support portion interlocked with the hub portion to block rotation of the hub portion with respect to the hub support portion and movement of the hub portion in the axial direction of the drive shaft with respect to the hub support portion, the hub support portion including a slider that is movable in a lateral direction perpendicular to the axial direction to allow the rotation of the hub portion with respect to the hub support portion while blocking the movement of the hub portion in the axial direction of the drive shaft with respect to the hub support portion.

9. The medical device according to claim 8, wherein the slider includes a body that is exposed through an opening in the hub support portion such that the body can be pressed to be moved in the lateral direction to allow the rotation of the hub portion with respect to the hub support portion while blocking the movement of the hub portion in the axial direction of the drive shaft with respect to the hub support portion.

10. The medical device according to claim 9, wherein the slider includes a body that is exposed through an opening in the hub support portion such that the body can be pressed to be moved in the lateral direction, a first contact surface that is in contact with one of the contact surfaces of the hub portion when the hub support portion is interlocked with the hub portion, and a second contact surface that is in contact with a distal surface of the hub portion when the hub support portion is interlocked with the hub portion.

11. The medical device according to claim 10, further comprising:
one or more springs against which the body is pressed when the body is moved in the lateral direction.

12. The medical device according to claim 11, wherein the springs include first and second springs having different spring constants, arranged in parallel.

13. The medical device according to claim 11, wherein the springs include first and second springs having different spring constants, arranged in series.

14. The medical device according to claim 10, wherein the slider includes a convex portion that protrudes through another opening in the hub support portion in a direction orthogonal to the lateral direction and the axial direction of the drive shaft, said another opening having an elongated shape to permit the convex portion to move in the lateral direction within said another opening as the slider moves in the lateral direction.

15. The medical device according to claim 14, wherein said another opening has varying widths at different positions along a length thereof, including widths at first and second positions that are each smaller than a width of the convex portion.

16. The medical device according to claim 15, wherein a third position of said another opening is between the first and second positions, and a width at the third position is greater than the width of the convex portion.

* * * * *